United States Patent [19]
Oren

[11] Patent Number: 6,143,752
[45] Date of Patent: Nov. 7, 2000

[54] METHOD FOR PREVENTING OR ARRESTING LIVER DAMAGE IN HUMANS

[76] Inventor: Ran Oren, 2600 Netherland Ave., Riverdale, N.Y. 10463

[21] Appl. No.: 09/126,967

[22] Filed: Jul. 31, 1998

Related U.S. Application Data
[60] Provisional application No. 60/054,518, Aug. 1, 1997.

[51] Int. Cl.[7] .................................................. A61K 31/505
[52] U.S. Cl. ............................................................ 514/274
[58] Field of Search ............................................. 514/274

[56] References Cited

PUBLICATIONS

DeMarco et al 96CA:115568, 1982.
Merk Index 10th Ed Windholtz ed # 4881, 1985.
Oren et al, Hepatology vol. 22 (4)(2) Abstract #1451, 1995.
Oren et al, Digestive Diseases & Sci, vol. 40 (9) pp 1941–45, 1995.
Oren et al, Idid vol. 42(7) pp 1433–37, 1997.
Orrego et al, New England J of Med Vol. 317(23) pp 1421 27, 1987.
Mishkin et al, Cancer Res vol 39 pp 2371–75, 1979.
Thompson et al, Gastroenterology vol. 106 pp 1342–43, 1994.
Bruck, R., et al. Hypothyroidism Minimizes Liver Damage and Improves Survival in Rats With Thiocetamide Induced Fulminant Hepatic Failure, *Hepatology,* 27:1013–1020 (1998).
*Goodman & Gilman's, The Pharmacological Basis of Therapeutics,* Antithyroid Drugs And Other Thyroid Inhibitors Chapter 56, 1397–1401, McGraw–Hill, New York (1996).
*Harrison's Principals of Internal Medicine,* pp. 1217–1224, 1660–1726, McGraw–Hill, New York (1998).
Kage, M., et al., Long–Term Evolution of Fibrosis From Chronic Hepatitis to Cirrhosis in Patients With Hepatitis C: Morphometric Analysis of Repeated Biopsies, *Hematology,* 25:1028–1031 (1997).
Kaplowitz, *Biliary Diseases,* Second Edition, pp. 139–140, 296–297, 330, 333, and 398–399 (1996).
Mishkin, S. et al. Increased Survival of Rats Bearing Morris Hepatoma 7800 after Induction of Hypothyroidism, *Cancer Research,* 39:2371–2375 (1979).

Oren, R. et al., Improved Liver Function in Cirrhotic Patients by Hypothyroidism, *Hepatology,* 22:469A (1995).
Oren, R. et al., Hemodynamic Effects of Hypothyroidism Induced by Methimazole in Normal and Portal Hypertensive Rats, *Digestive Diseases and Sciences,* 40:1941–1945 (1995).
Oren, R., et al. Methimazole Slows Hepatocyte Streaming in Rats, *Digestive Diseases and Sciences,* 42:1433–1437 (1997).
Oren, R., et al. Inhibition of Experimentally Induced Cirrhosis in Rats by Hypothyroidism, *Hepatology,* 24:419–423 (1996).
Oren R. et al., Hemodynamic Effects of Hypothyroidism Induced by Methimazole in Normal and Portal Hypertensive Rats, *Digestive Diseases and Sciences,* 40:941–1945 (1995).
Orrego, H. et al. Long–Term Treatment of Alcoholic Liver Disease with Propylthiouracil, *The New England Journal of Medicine,* 317:1421–1427 (1987).
Raheja, K. et al. Protective Effect of Propylthiouracil Independent of its Hypothyroid Effect on Acetaminophen Toxicity in the Rat, *Journal of Pharmacology and Experimental Therapeutics,* 220:427–432 (1982).
Singer, D., et al. Methimazole Prevents Induction of Experimental Systemic Lupus Erythematosus in Mice, *The Journal of Immunology,* 154:873–880 (1994).
Thompson, N. Reversible Jaundice in Primary Biliary Cirrhosis Due to Hyperthyroidism, *Gastroenterology,* 106:1342–1343 (1994).
Williams, K., et al. Fifty Years of Experience with Propylthiouracil–Associated Hepatotoxicity: What Have We Learned?, *Journal of Clinical Endocrinology and Metabolism,* 82:1727–1733 (1996).

*Primary Examiner*—Russell Travers
*Attorney, Agent, or Firm*—Darby & Darby

[57] ABSTRACT

The invention provides methods for treating liver disease by inducing a hypothyroid state using (i) drugs, e.g., PTU, methimazole, lithium or carbimazole; (ii) surgery; or, (iii) radiation, e.g., $^{127}$I or $^{131}$I. The liver diseases that can be treated using the methods of the invention include: infectious hepatitis, such as (i) viral hepatitis resulting from infection with hepatitis A, D, C, D, E, or G; or (ii) parasitic hepatitis resulting from infection with *Schistosoma mansoni, Schistosoma hematobium* or *Schistosoma japonicum*; or (iii) autoimmune disease, e.g., (a) autoimmune hepatitis or (b) primary biliary cirrhosis.

20 Claims, 2 Drawing Sheets

METHOD FOR PREVENTING OR ARRESTING LIVER DAMAGE IN HUMANS

This Application claims priority from Provisional Application No. 60/054,518, filed Aug. 1, 1997 now abandoned.

FIELD OF THE INVENTION

This invention is directed to methods for preventing, attenuating, retarding or arresting liver damage caused by infection or autoimmune-mediated diseases.

BACKGROUND OF THE INVENTION

The liver is the target of attack for a wide range of diseases. These diseases include infectious, autoimmune, as well as non-infectious processes such as chemicals. Examples of infectious diseases include: (i) viral hepatitis, e.g., hepatitis A, B, C, D, E, and G and (ii) parasitic hepatitis, e.g., *Schistosoma mansoni, Schistosoma hematobium*, and *Schistosoma japonicum*. (*Harrison's Principles of Internal Medicine*, Fauci et al. eds., 1998, pgs 1660–1725). Examples of noninfectious diseases affecting the liver, include autoimmune diseases, such as, (i) autoimmune hepatitis and (ii) primary biliary cirrhosis. (*Harrison's Principles of Internal Medicine*, Fauci et al. eds., 1998, pgs 1701–1709). Regardless of whether the attack on the liver is infectious, autoimmune or noninfectious, the liver responds to injury by pouring inflammatory cells into the site of attack. The types of inflammatory cells entering the site of attack consist primarily of macrophages and neutrophils. After entry into the site of injury, the cells release various inflammatory cytokines, such as tumor necrosis factor (TNF). These cytokines mediate the local inflammatory response by inducing local changes, for example, proliferation of fibroblasts or vasodilation.

If left untreated, repeated, chronic damage to the liver from infection, autoimmune disease or any other noninfectious processes causes scarring or fibrosis. This is a direct consequence of local proliferation of fibroblasts. (Kaplowitz, *Biliary Diseases*, pg. 139, Williams & Wilkins, 1992). In the case of the liver, the end-stage of fibrosis is cirrhosis. Pathologically, cirrhosis is defined as extensive fibrosis in the liver in association with the formation of regenerative nodules. Cirrhosis is the final common pathway for many, if not all, types of chronic liver damage and is typically progressive. (Kaplowitz, *Biliary Diseases*, pg. 140, Williams & Wilkins, (1992).

Because of the morbidity and mortality of untreated liver disease, either of an infectious or autoimmune nature, there is a need for developing effective treatments for preventing or reducing liver fibrosis and cirrhosis. Anti-thyroid hormone therapy offers a new way to treat the damaging effects of these diseases on the liver. Orrego et al. (*New Eng. J. Med.* 317(3)1427 (1987)) described long-term treatment of alcoholic liver disease with propylthiouracil (PTU), an anti-thyroid drug that blocks formation of thyroid hormones. (Goodman & Gilman, *The Pharmacological Basic of Therapeutics*, McGraw-Hill, pgs. 1398–1399 (1996)). The authors report a significant reduction in the mortality of patients with alcoholic liver disease. Other studies found that PTU protects the liver from damage resulting from chemical injury. For example, Yamada et al. (*J. Clin. Invest.* 67688 (1981)) and Raheja et al. (*J. Pharm. Exper. Therapeutics* 220:427 (1982)) found that PTU protected rats from acetaminophen-induced hepatocytotoxicity.

However, before the present invention, there had been no attempt to associate a hypothyroid condition with treating liver damage caused by infection. More particularly, there had been no attempt to treat humans afflicted with infectious diseases such as hepatitis. This was due, in part, to the fact that PTU is a hepatotoxic material that can cause severe liver damage, including death, and the damage to the liver in alcoholic or chemically-induced liver disease is completely different from that of either virally-induced or autoimmune mediated liver disease.

First, using PTU to induce a hypothyroid-state is fraught with danger. Williams et al. showed that PTU-associated heptotoxicity is a well-recognized life-threatening complication of antithyroid drug treatment. (*J. Clin. Endocrin. & Metabol.* 82:1727 (1997)). Although the incidence of PTU-associated heptotoxicity was less than 0.5%, PTU-hepatoxicity can occur in all age groups and is often fatal. Consequently, the effects on the liver of treating patients with PTU are unpredictable.

Second, the pathophysiology of chemically-induced, i.e., alcohol, liver disease is completely different from damage caused by viral or autoimmune liver disease. Specifically, damage to the liver caused by alcohol comprises hypoxic damage to the central vein area which is accompanied by fatty changes to the liver. In contrast, damage to the liver caused by infectious or autoimmune disease comprises infiltration of inflammatory cells near the portal zone. (Kaplowitz, *Biliary Diseases*, pg. 140, Williams & Wilkins, 1992). Because the pathology of viral or autoimmune liver disease is completely different from either alcoholic or acetoaminophen-induced liver disease and in view of the hepatotoxicity of using PTU, prior to the present invention there was no reason to believe that inducing hypothyroidism could be used to treat damage to the liver caused by infection or autoimmune disease.

Because of the large number of affected individuals, there exists an overwhelming need to effectively treat damage to the liver resulting from infectious or autoimmune diseases. To date, there is no satisfactory treatment for preventing or reversing the fibrotic process that results from this type of injury to the liver. (Kaplowitz, *Biliary Diseases*, pg. 330, Williams & Wilkins, 1992). This need is clearly shown by the magnitude of the clinical problem worldwide. For example, there are more than 300 million carriers of hepatitis B. (Kaplowitz, *Biliary Diseases*, pg. 330, Williams & Wilkins, 1992). Every cancer patient being treated for leukemia or Hodgkin's lymphoma is particularly susceptible to infection with hepatitis B. (Kaplowitz, *Biliary Diseases*, pg. 330, Williams & Wilkins, 1992). In some tropical countries, the prevalence of hepatitis B is as high as 30% of the adult population. Moreover, infection with hepatitis B places the patient at risk for developing heptocellular carcinoma. (Kaplowitz, *Biliary Diseases*, pg. 399, Williams & Wilkins, 1992). Hepatitis C is the major form of transfusion-hepatitis and the number of reported cases worldwide is growing rapidly. (Kaplowitz, *Biliary Diseases*, pg. 333, Williams & Wilkins, 1992). In the general population, hepatitis C is responsible for over half the cases of acute viral hepatitis. (Kaplowitz, *Biliary Diseases*, pg. 297, Williams & Wilkins, 1992). The number of people infected with the parasitic form of hepatitis caused by Schistosoma is staggering. Worldwide over 200 million people are infected with this parasite. (*Harrison's Principles of Internal Medicine*, Fauci et al. eds., 1998, pgs 1217–1224). Schistosoma causes significant fibrotic damage to the liver. (*Harrison's Principles of Internal Medicine*, Fauci et al. eds., 1998, pgs 1217–1224).

Therefore, there is a long-standing need in the art for effective treatments for preventing or arresting liver damage resulting from infection or autoimmunity.

The present invention relates to methods for treating liver damage by making patients biochemically hypothyroid. The patients can be made biochemically hypothyroid using drugs such as PTU, partial thyroidectomy or by radiation with radioactive iodine.

SUMMARY OF THE INVENTION

The present invention is based on the discovery that induction of biochemical hypothyroidism in patients suffering from infectious or autoimmune liver disease prevents or arrests liver damage. The invention provides methods for treating liver disease by inducing a hypothyroid state using (i) drugs, e.g., PTU, methimazole, lithium or carbimazole; (ii) surgery; or, (iii) radiation, e.g., $^{127}$I or $^{131}$I. The liver diseases that can be treated using the methods of the invention include: infectious hepatitis, such as, (i) viral hepatitis resulting from infection with hepatitis A, D, C, D, E, or G; or (ii) parasitic hepatitis resulting from infection with *Schistosoma mansoni, Schistosoma hematobium* or *Schistosoma japonicum*; or (iii) autoimmune disease, e.g., (a) autoimmune hepatitis or (b) primary biliary cirrhosis. Harmful side effects of hypothyroid-inducing agents can be mitigated or avoided by (i) using lower doses of hypothyroid agents than previously considered and (ii) closely monitoring liver function.

DETAILED DESCRIPTION OF THE INVENTION

Figure 1:
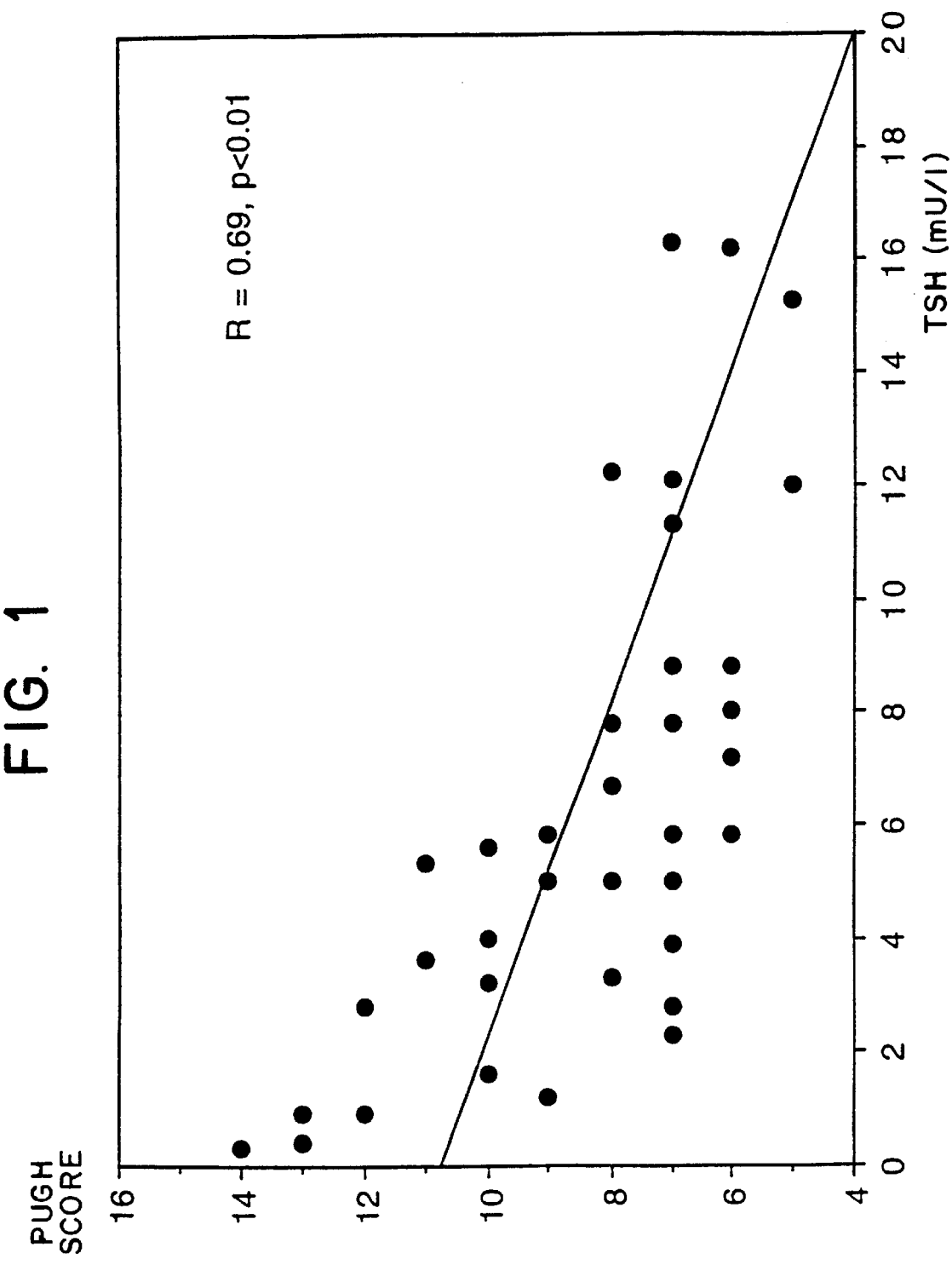
FIG. 1 is an illustration of the correlation between Pugh score and serum thyroid stimulating hormone (TSH) levels in the hypothyroid and euthyroid state.

All patent applications, patents and literature cited in this specification are hereby incorporated by in their entirety. In the case of conflict, the present descriptions, including definitions will control.

DEFINITIONS

1. "Low normal thyroid function" as used herein refers to a clinical condition in which the thyroid hormones T3 and T4 are at their lowest normal range (T3=1.1–2.9 nmol/L and T4=64–154 nmol/L) and in which TSH is mildly elevated above normal. Normal levels for TSH are 0.4–5 mU/L. (Oren et al. *Dig. Dis. Sci.* 40: 1941 (1995): hormone levels are determined using a chemiluminescent assay as described).

2. "Biochemical hypothyroid state" or "biochemical hypothyroidism" as used herein refers to a condition in a patient in which TSH is elevated at least 6-fold (six-fold) above normal, while T3 and T4 remain low normal.

3. "Subtotal thyroidectomy" as used herein refers to partial surgical resection of the thyroid in a patient with sparing of the parathyroid glands. Total thyroidectomy refers to the complete surgical removal of the thyroid gland.

4. Viral hepatitis as used herein refers to hepatitis A, D, C, D, E, or G.

5. Liver damage as used herein refers to the inflammatory response of the liver to injury, which results in an influx of macrophages and neutrophils into the injured site. Accompanying this influx of inflammatory cells is a local proliferation of fibroblasts as well as inflammatory cytokines such as TNF.

6. Fibrosis of the liver as used herein refers to a proliferation of fibroblasts with accompanying scar tissue formation in the liver. Fibrosis is determined by liver biopsy and staged according to Kage et al.: stage I—none to mild stage II—mostly periportal, stage III—septal, and stage IV—full blown cirrhosis. (*Hepatology* 25:1028 (1995)).

7. Cirrhosis as used herein refers to a pathologically defined entity that is associated with a spectrum of characteristic clinical manifestations in a patient. The cardinal pathologic features reflect irreversible chronic injury of the liver and include extensive fibrosis in association with formation of regenerative nodules. Cirrhosis is the final common pathway for most types of chronic liver damage.

8. Prevention of liver damage as used herein refers to blocking the fibrotic proliferative response, i.e., the progression from stage I to higher stages, e.g., stage II, III or IV (see Kage, et al. supra.).

9. Reduction or amelioration of liver damage as used herein refers to a decreased proliferative response of fibroblasts in response to damage, i.e., regression from a higher stage to a lower stage, e.g., change from stage III to stage II (see, Kage et al. supra.).

10. Treatment as used herein refers to prevention, reduction, or amelioration of liver damage in a human.

11. Liver function tests as used herein include, but are not limited to measurement of alanine amino transferase (ALT), alkaline phosphatase (ALK.P.), bilirubin, prothrombin (PT), and albumin (ALB).

12. "Clinical Hypothyroidism" as used herein is manifested by (i) bradycardia (<25% the base line heart rate), (ii) constipation and (iii) decreased peripheral reflexes.

The present invention is based on the unexpected finding that agents or methods which induce a biochemical hypothyroidism by lowering the thyroid hormone blood levels without inducing clinical hypothyroidism can treat damage to the liver, such as that caused by infection of the liver or autoimmune disease of the liver. Prior to the present invention, there was no disclosure or suggestion that inducing a biochemical hypothyroid state in patients would effectively treat liver damage resulting from infection or autoimmune diseases. The diseases encompassed by this invention include without limitation viral and parasitic hepatitis as well as autoimmune hepatitis.

A large number of different viral diseases affecting the liver are encompassed by the invention, i.e., the liver damage caused by these diseases can be prevented, attenuated, retarded, or arrested using the invention. These viruses include without limitation, hepatitis A, hepatitis B, hepatitis C, hepatitis D, hepatitis E, and hepatitis G. Hepatitis C is a particular problem there being at this time no known treatment or vaccine against the disease.

A large number of parasitic diseases affecting the liver are also encompassed by this invention. These parasitic diseases include without limitation, *Schistosoma mansoni, Schistosoma hematobium* and *Schistosoma japonicum*.

Also encompassed by this invention are all T-cell mediated diseases which affect the liver. Autoimmune damage from T cells is mediated directly by T cytotoxic cells and indirectly T helper cells. In general, autoimmunity is mediated by these two types of T cells. (Janeway et al. *Immunobiology*, Current Biology Limited, 1997). Autoimmune diseases encompassed by this invention include without limitation autoimmune hepatitis and primary biliary cirrhosis. Autoimmune hepatitis (formerly called autoimmune chronic active hepatitis) is a chronic disorder characterized by continuing hepatocellular necrosis and inflammation, usually with fibrosis, which tends to progress to cirrhosis and liver failure. This type of chronic hepatitis may have a 6-month mortality of as high as 40 percent. The prominence of extrahepatic features of autoimmunity as well as seroimmunologic abnormalities in this disorder supports an autoimmune process in its pathogenesis.

Primary biliary cirrhosis (PBC) is an autoimmune disease of the intrahepatic or biliary system. PBC is associated with impaired bile secretion. Autoimmune antibodies and T cells appear to mediate tissue damage to the liver.

The present invention has several important applications. It can be used to treat liver damage incident to infectious or autoimmune disease. It can also be used as a bridge for patients waiting for liver transplant. Bridging patients is accomplished by maintaining the patient in a biochemical hypothyroid state until a suitable liver is found which is available for transplant. By maintaining them in a biochemical hypothyroid condition, patients ineligible for liver transplants can survive for longer lengths of time. The invention can also be used to arrest liver disease at a very early stage by keeping patients in a biochemical hypothyroid state in which low normal thyroid function is maintained.

The present invention is based on the discovery that induction of biochemical hypothyroidism in patients suffering from infectious or autoimmune liver disease retards, attenuates or prevents liver damage. The invention provides methods for treating liver disease by inducing a hypothyroid state using (i) drugs, e.g., PTU, methimazole, lithium or carbimazole; (ii) surgery; or, (iii) radiation, e.g., $^{127}$I or $^{131}$I. The liver diseases that can be treated using the methods of the invention include: infectious hepatitis, such as (i) viral hepatitis resulting from infection with hepatitis A, D, C, D, E, or G; or (ii) parasitic hepatitis resulting from infection with *Schistosoma mansoni, Schistosoma hematobium* or *Schistosoma japonicum*; or (iii) autoimmune disease, e.g., (a) autoimmune hepatitis or (b) primary biliary cirrhosis.

Agents suitable for use in the present invention, are those pharmaceutically acceptable agents which lower the levels of circulating thyroid hormone and include by way of example, and without limitation: PTU, methimazole, lithium, carbimazole as well as radioactive compounds, such as $^{127}$I and $^{131}$I. These agents are generally well known to those skilled in the art and commercially available. In instances where low thyroid function is to be permanently maintained, a partial or total thyroidectomy can also be performed. In order to maintain basal thyroid function, the levels of thyroid hormone can be added back using supplements which contain T3 and T4. Preferred administration frequency of the hypothyroid compound depends on the compound employed but is generally daily. In general, an effective amount for lowering circulating thyroid hormone level of the pharmaceutically acceptable agent should be administered daily for at least three months to determine effectiveness of the administered dose of hypothyroid agent in a particular patient. The dose given to the patient can then be adjusted based upon the patient's circulating thyroid hormone level. Treatment may continue for as long as the benefits to the patient persist, or until a suitable liver transplant is found. In general, (i) an effective amount of methimazole for lowering circulatory thyroid hormone is between 10 and 45 mg per day, preferably between 10 and 30 mg per day, and most preferably 20 mg per day, and (ii) an effective amount of PTU for lowering circulatory thyroid hormone is between 100 and 450 mg per day, preferably between 100 and 300 mg per date, and most preferably 200 mg per day. The exact dose given to a particular patient will obviously be adjusted depending on the patients disease state, condition, and level of circulatory thyroid hormones.

In practicing the present invention, patients with known viral or immune liver disease are enrolled. The baseline severity of the liver disease will determined by clinical and laboratory evaluation. This includes assessment of quality of life, activities, weakness, wasting, esophageal varices, ascites and encephalopathy as well as an analysis of liver function tests. Thyroid function tests including, serum levels of TSH, T3 and T4 will also be examined. The patient is given PTU (100–150 mg, administered 1–3 times a day) or methimazole (10–15 mg, administered 1–3 times a day) for at least three months. Benefits of treatment will be assessed by follow-up of liver function with clinical and laboratory assessment, performed every week for up to 1 month, every 2 weeks up to 3 months and every month thereafter. Side effects will be minimized by avoiding induction of clinical hypothyroidism. This result is achieved by maintaining TSH blood levels between 5–30 m U/L. Liver function will be monitored as described and liver biopsy will be considered in specific cases. Liver function tests will be evaluated serially to determine whether there is an improvement in these tests in response to treatment. Improvement in liver function comprises a 10% decrease in all liver function tests towards normal ranges as well as a decrease in inflammation or fibrosis as determined by liver biopsy. The desired degree of the induced hypothyroid condition is the minimum effective hypothyroid state required to reduce or arrest further liver damage.

In practicing the present invention, the levels of TSH are preferably six times normal, whereas the T3 and T4 levels are not more than 10–15% greater than normal ranges. Liver function is monitored by measuring the following liver enzymes, (i) ALT, (ii) Alk. P., (iii) ALB, (iv) PT, and (v) bilirubin, using standard clinical laboratory techniques. The amount of hypothyroid agent administered can be adjusted accordingly by the clinician treating the patient using the well known and medically accepted criteria for liver and thyroid function.

The following examples are intended as non-limiting illustrations of the present invention.

EXAMPLE 1

ANALYSIS OF PATIENTS WITH VARIOUS FORMS OF LIVER DISEASE: COMPARISON TO THYROID FUNCTION

The following study was performed to assess liver function in patients with various forms of liver disease and to correlate liver function with thyroid status.

A. Methods

Patients—The files of patients in the Hadassah University Hospitals, Jerusalem, and the University Medical Centers of Tel Aviv, Holon and BeerSheba, between the years 1980–1990, with biopsy proven liver cirrhosis of different etiologies, including, hepatitis C, immune chronic hepatitis or ICA, primary biliary cirrhosis or PBC, alcohol or cryptogenic (i.e., unknown cause) were evaluated for thyroid function.

Study design—Eligible patients were asked to visit the outpatient clinic for evaluation at least twice a year. The evaluation included a medical history, physical examination and complete blood count, thyroid and liver function tests. They were also instructed to call the clinic in case of any unusual medical problem. Since all patients suffered from documented active cirrhosis repeated liver biopsy was not a part of the study protocol. Cirrhosis was defined by the acceptable criteria of liver biopsy. Thyroid status was defined on the basis of TSH level. The minimum TSH was 30% above the normal range according to the normal values in each laboratory.

Statistical analysis—Patients were evaluated as individual cases and in groups. T-test was used in order to compare between the hypo and euthyroid groups of patients. Correlation between the difference from the baseline of TSH blood levels and functional, transport and synthetic liver function tests. Results are expressed as means and standard deviations. Results are considered significant at $p<0.05$. Each patient served as his own control.

Table 1 shown below provides the results of this study.

Hypothyroidism was either primary (9 patients), immune mediated (5) or induced, i.e., either drug-2 or surgery-2. All hypothyroid patients were on thyroxine treatment.

When all euthyroid patients were compared to the hypothyroid group, identified by elevated TSH, a significant decrease in ALT (mean ALT 179±30 vs 61±9 u/l respectively, $p<0.001$), Alkaline phosphatase (AP) (124.7±49.0 vs 78.4±19.8, u/l $p<0.0001$), albumin (3.04±0.16 vs 3.64±0.31 g/l, $p<0.001$) and bilirubin (1.61±0.78 vs 1.15±0.41 mg %, $p<0.01$) were found. Prothrombin (PT) was also found to be significantly different (54.1±3.8 Vs 60.4±6.2% $p<0.001$). There was also an inverse correlation between the Pugh score and TSH level, showing that the severity of liver disease was lower in

TABLE 1

Patients characterization and epidemiology

| No. | Sex | Age (y) | A. Cir | Hypo. | Drugs | V | A | E | Comm | C-P |
|---|---|---|---|---|---|---|---|---|---|---|
| 1 | M | 69 | HCV | Tx-Hr | PTU | + | − | − | | B |
| 2 | M | 72 | Crp | s/p T | Thx | + | − | − | | B |
| 3 | M | 60 | HCV | UK | Thx | + | + | − | | B |
| 4 | M | 75 | HBV | Tx-Hr | Thx | + | + | − | $I^{RA}$ | C |
| 5 | F | 56 | HCV | s/p T | Thx | − | − | − | | A |
| 6 | F | 35 | HCV | Imm | Thx | − | − | − | | A |
| 7 | M | 61 | PBC | Imm | Thx | − | − | − | | A |
| 8 | F | 50 | PBC | Imm | Thx | + | − | − | | A |
| 9 | F | 30 | HBV | UK | Thx | + | − | − | | A |
| 10 | F | 45 | AIH | Imm | Thx | − | − | − | | A |
| 11 | F | 78 | Crp | UK | Thx | + | + | + | | B |
| 12 | F | 65 | HCV | UK | Thx | + | − | − | | A |
| 13 | F | 69 | Crp | UK | Thx | * | + | + | S | B |
| 14 | F | 44 | AIH | Imm | Thx | + | − | − | | A |
| 15 | F | 68 | HBV | UK | Thx | * | + | + | S | B |
| 16 | F | 41 | HBV | UK | Thx | * | + | + | | C |
| 17 | M | 64 | Alc | UK | Thx | * | + | + | | B |
| 18 | F | 56 | HCV | UK | Thx | − | − | − | − | B |

A. Cir-active cirrhosis
Hypo-hypothyroidism
Find-Physical findings
s/p T-s/p thyroidectomy
Imm-immune
F-encephalopathy
HBV-hepatitis B virus
HCV-hepatitis C virus
Tx-Hr-treated hyperthyroidism
V-varices *-bleeding
Crp-cryptogenic
Fluc-fluctuations
S-spontaneous bacterial peritonitis
Alc-alcoholic liver disease
AIH-autoimmune hepatitis
M-male
F-female
Comm-comments
UK-etiology unknown
A-ascites
Thx-thyroxine
C-P-Child's Pugh Results—Between 1991–1994, eighteen patients (12 women and 6 men, mean age 59±24 years) met the inclusion criteria and were enrolled in the present study. Patients characterization, epidemiology and Child's-Pugh score are summarized in table 1. A spectrum of different etiologies were responsible for the cirrhosis: (i) 9 had hepatitis C virus (HCV); (ii) 2 had hepatitis B virus (HBV); (iii) 2 had inflammatory chronic hepatitis (ICH); (iv) 2 had primary biliary cirrhosis; (v) 1 had alcoholic liver disease; and (vi) 2 had cryptogenic cirrhosis. Most patients were categorized as Child's A or B (A-8, B-8, C-2). (Kaplowitz, *Biliary Diseases*, pg. 139–140, Williams & Wilkins, 1992).

patients where the TSH level was high, e.g., six-fold increased above normal (FIG. 1).

EXAMPLE 2

CASE REPORT OF A PATIENT SUFFERING FROM CRYPTOGENIC CIRRHOSIS

The following detailed analysis was performed of an individual patient in order to more closely evaluate the effect of thyroid status on liver function.

Methods—A 72-year-old male with chronic ischemic heart disease and essential hypertension (treated with diltiazem and nitrates) underwent thyroidectomy at the age of 22. He did not take thyroxine regularly and therefore has fluctuations in the thyroid state. For 22 years he was known to suffer from cryptogenic cirrhosis. The patient experienced deterioration in liver function whenever he was euthyroid and improvement during periods when he was hypothyroid.

EXAMPLE 3

CASE REPORT OF A PATIENT SUFFERING FROM CIRRHOSIS DUE TO INFECTION WITH HEPATITIS C (HCV)

The following detailed analysis was performed of an individual patient in order to more closely evaluate the effect of thyroid status on liver function.

Methods—A 60-year-old male with 12 years of cirrhosis due to HCV infection, stable ascites, esophageal varices and hypothyroidism. The patient compliance to therapy was poor and during the 9 years prior to the study period his TSH levels were elevated. Nevertheless, despite having advanced liver disease his clinical condition was stable. Shortly after stabilization of the thyroid state, he experienced two episodes of hepatic deterioration including variceal bleeding and encephalopathy. During 18 months of follow up he was subclinically hypothyroid with stable liver function.

Figure 2:
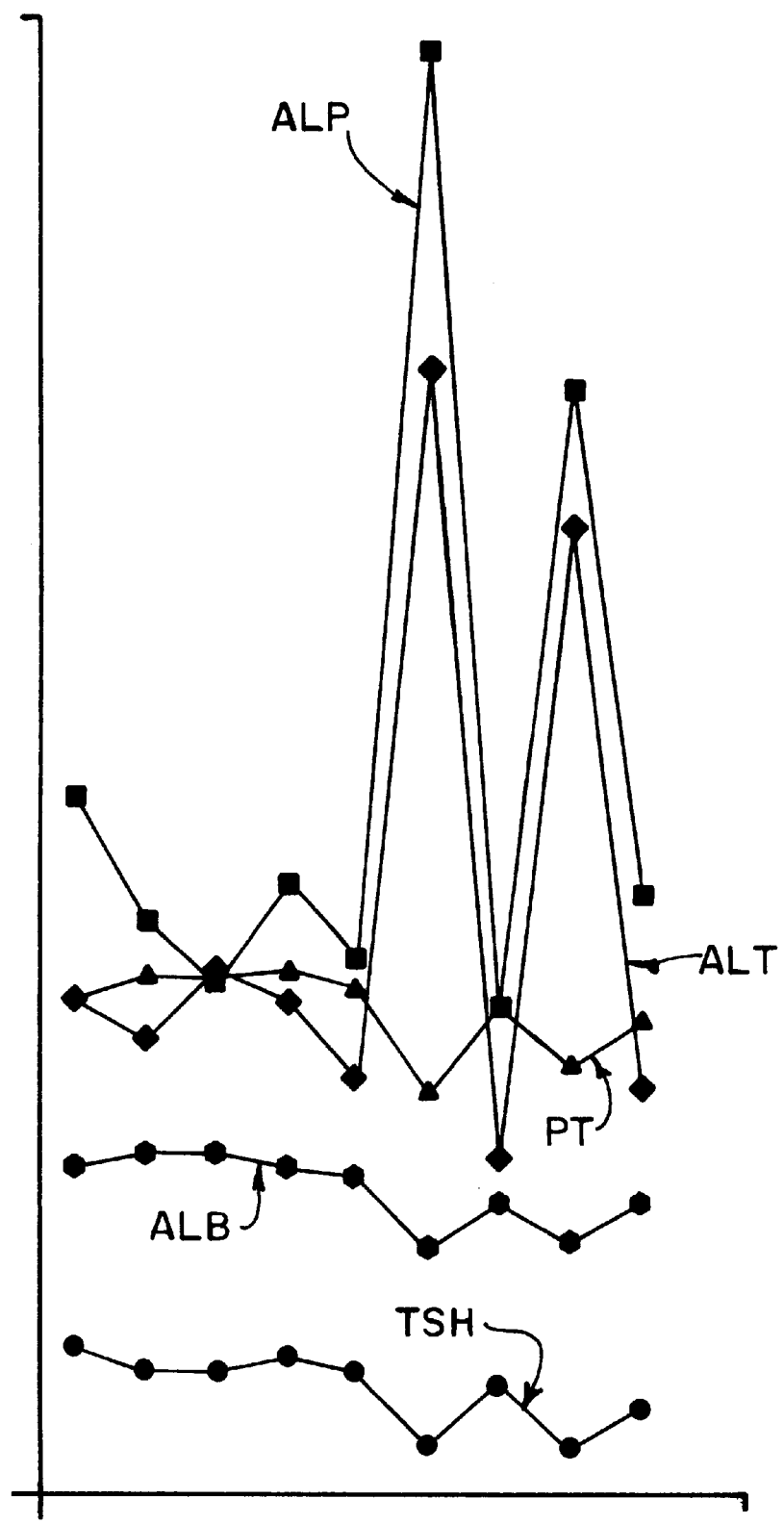
FIG. 2 is a graphical illustration of liver function of a single patient during periods of hypothyroid as compared to a normal thyroid state.

As shown in FIG. 2 when the patient's levels of TSH dropped there was an immediate deterioration in liver function as shown by the increase in circulating levels of ALT and ALP.

EXAMPLE 4

TREATMENT OF CONCANAVALIN A INDUCED HEPATITIS BY INDUCTION OF HYPOTHYROIDISM

The present study was conducted to find out whether hypothyroidism could prevent the development of acute T-cell mediated hepatic damage induced in mice by con A. T cell mediated liver disease is a model for autoimmune liver disease. (Manns et al. *Gastroenterology* 106:1676 (1994)). The results obtained with this animal model can be easily extrapolated to humans suffering from autoimmune liver disease.

Methods

Animals—6–8 weeks-old male Balb/C mice were maintained in the Animal Breeding Center of the Wolfson Hospital, Israel. Treatment of the mice was in accordance with guidelines of the Tel-Aviv University.

Acute liver injury—Mice were inoculated with 10 mg/kg Con A (Sigma. St. Louis, Mo.) in 250 μl phosphate buffered saline (PBS) administered via their tall veins. (Tiegs et al. *J Clin Invest.* 90:196 (1992)).

Hypothyroidism was induced by the administration of either methimazole (MMI) 0.04% or PTU 0.05% in drinking water for two weeks prior to Con A administration. Surgical thyroidectomy was performed with the animals under chloralhydrate anesthesia 2 weeks prior to the induction of Con A hepatitis. All mice had free access to tap water during the week before Con A administration. Hypothyroidism was confirmed by measuring TSH blood levels. PTU, MMI and surgical removal of the thyroid gland were each followed by significant TSH elevation (1.7±0.3, 1.9±0.5, 1.4±0.4 mmo/$L^{-1}$, P=nonspecific (NS)) as compared to the untreated control groups (0.15±0.03, 0.12±0.03, 0.21±0.06 mmo/$L^{-1}$, P=NS) respectively ($p<0.001$).

Evaluation of liver injury—Six hours after inoculation of Con A, mice were bled and then sacrificed. The extent of liver injury was analyzed by determining the serum levels of the following active enzymes: ALT, AST and Lactate dehydrogenase (LDH) as previously described. (Greco et al. *Vet-Clin-North-Am-Small-Anim-Pract* 24:765 (1994)). TNF levels were measured in a bioassay using the murine fibrosarcoma cell line WEHI 164 clone 13 according to the Espevik et al. (*J. Immunol Methods* 95:99 (1995)).

Analysis of liver histopathology—For semiquantitative analysis, the midsections of the left lobes of the excised livers were processed for light microscopy. Thus processing consisted of fixing the specimens in a 5% neutral formal solution, embedding the specimens in paraffin, slicing sections 5 μm in thickness and staining the sections with hematoxylin and eosin (H&E). The tissue slices were scanned and scored semiquantatively by two expert pathologists who were not aware of sample assignment to experimental group. The degrees of inflammation were expressed as the mean of 10 different fields within each slide that had been classified on a scale of 0–3 (normal—0, mild—1, moderate—2, severe—3).

Results—Typical liver injury, as manifested by significant elevations of the AST, ALT and LDH levels in the serum was observed in the con A treated, but not in the untreated mice (Table 2). Serum levels of ALT, AST and LDH in normal mice were 40±10, 70±15 and 1800±200 IU/l respectively. Following Con A administration, the levels were increased to 1499±118, 1399±17 and 9536±434 IU/l. In the hypothyroid groups, levels of those hepatic enzymes decreased significantly ($p<0.001$).

TNF levels—The serum levels of TNF, were also significantly lower in the hypothyroid Con A treated groups as compared with Con A alone (135±15 vs 2500±250 pg/ml).

Liver histology evaluation—Two pathologists, blindly and independently examined liver biopsies specimens from both groups, and found that while Con A caused severe hepatic damage the livers from the hypothyroid groups were only mildly damaged (data not shown).

TABLE 2

The effect of hypothyroidism on liver enzymes

|  | ALT (IU/l) | AST (IU/l) | LDH (IU/l) |
| --- | --- | --- | --- |
| Control | 40 ± 10 | 70 ± 15 | 1800 ± 200 |
| Con A | 1499 ± 118 | 1399 ± 17 | 9536 ± 434 |
| PTU | 58 ± 9* | 98 ± 7* | 1560 ± 124* |
| MMI | 72 ± 12* | 56 ± 11* | 1230 ± 145* |
| Thyroidectomy | 45 ± 17* | 67 ± 12* | 1900 ± 120* |
| Con A + PTU | 234 ± 11* | 229 ± 14* | 2178 ± 714* |
| Con A + MMI | 78 ± 10* | 156 ± 83* | 2170 ± 562* |
| Con A + Thyroidectomy | 228 ± 25* | 69 ± 16* | 1817 ± 52* |

*$P < 0.001$ (compared to Con A)

EXAMPLE 5

TREATMENT OF PATIENTS SUFFERING FROM HEPATITIS B

A patient diagnosed with hepatitis B by positive expression of HbsAg (hepatitis surface antigen) using enzyme-linked-immunoabsorbance assay (ELISA) will be treated with PTU to induce a biochemical hypothyroid condition. The patient will be administered 100 to 150 mg of PTU, three times daily for up to three months. Thyroid function tests will be monitored weekly by measuring T3, T4 and TSH. The desired range of T3 and T4 is 10–15% of the normal range and the desired range of TSH is six times normal. Liver function will be monitored weekly using the standard battery of liver function tests as well as blood counts to avoid bone-marrow depression from PTU.

What is claimed:

1. A method for treating liver damage associated with infection or autoimmune disease in a patient comprising inducing in a patient afflicted with said infection or autoimmune disease and in need of such treatment by administering a therapeutically effective amount of propylthiouracil in quantities to effect a biochemical hypothyroid condition and maintaining said condition for the duration of the treatment of said patient.

2. The method of claim 1 wherein the infection is viral hepatitis.

3. The method of claim 2 wherein the infection is selected from a group consisting of hepatitis A, hepatitis B, hepatitis C, hepatitis D, hepatitis E, and hepatitis G.

4. The method of claim 1 wherein the infection is a parasitic hepatitis.

5. The method of claim 4 wherein the infection is selected from the group consisting of *Schistosoma mansoni, Schistosoma haematobium*, and *Schistosoma japonicum*.

6. The method of claim 1 wherein the autoimmune disease is selected from a group consisting of autoimmune hepatitis and primary biliary cirrhosis.

7. The method of claim 1 wherein the effective amount of the hypothyroid agent is sufficient to cause an increase in thyroid stimulating hormone of about six-fold above the normal range.

8. The method of claim 1 further comprising continuing said administration for a period of time of at least three months.

9. The method of claim 1 wherein the hypothyroid agent effects a partial thyroidectomy.

10. A method for and treating liver damage associated with T-cell mediated disease in a patient comprising inducing in a patient afflicted with said T-cell mediated disease and in need of such treatment by administering a therapeutically effective amount of propylthiouracil in quantities to effect a biochemical hypothyroid condition and maintaining said condition for at least three months.

11. The method of claim 10 wherein the effective amount of the hypothyroid agent is sufficient to cause an increase in thyroid stimulating hormone of about six-fold above the normal range.

12. The method of claim 10 further comprising continuing said administration for a period of time of at least three months.

13. The method of claim 10 wherein the hypothyroid agent effects a partial thyroidectomy.

14. A method for treating liver damage associated with infectious disease in a patient comprising inducing in a patient afflicted with said infectious disease and in need of such treatment by administering a therapeutically effective amount of propylthiouracil in quantities to effect a biochemical hypothyroid condition and maintaining said condition at least three months.

15. The method of claim 14 wherein the infection is viral hepatitis.

16. The method of claim 15 wherein the infection is selected from a group consisting of hepatitis A, hepatitis B, hepatitis C, hepatitis D, hepatitis E, and hepatitis G.

17. The method of claim 14 wherein the infection is a parasitic hepatitis.

18. The method of claim 17 wherein the infection is selected from the group consisting of *Schistosoma mansoni, Schistosoma haematobium*, and *Schistosoma japonicum*.

19. The method of any one of claims 1, 12 or 18 wherein the amount of PTU is from about 100 mg to about 450 mg of PTU.

20. The method of any one of claims 1, 12 or 18 wherein PTU is administered three times per day for about three months.

* * * * *